(12) United States Patent
Wen

(10) Patent No.: US 12,350,516 B2
(45) Date of Patent: Jul. 8, 2025

(54) METHOD, CONTROLLER AND SYSTEM FOR CONTROLLING DOSE IN RADIOTHERAPY

(71) Applicants: OUR UNITED CORPORATION, Xi'an (CN); Shenzhen OUR New Medical Technologies Development Co., Ltd., Shenzhen (CN)

(72) Inventor: Xiaojuan Wen, Xi'an (CN)

(73) Assignee: Shenzhen OUR New Medical Technologies Development Co., Ltd., Shenzhen (CN)

( * ) Notice: Subject to any disclaimer, the term of this patent is extended or adjusted under 35 U.S.C. 154(b) by 0 days.

(21) Appl. No.: 18/434,987

(22) Filed: Feb. 7, 2024

(65) Prior Publication Data

US 2024/0173567 A1    May 30, 2024

Related U.S. Application Data

(63) Continuation of application No. 17/475,078, filed on Sep. 14, 2021, now Pat. No. 11,918,829.

(30) Foreign Application Priority Data

Sep. 15, 2020   (CN) .......................... 202010970428.4

(51) Int. Cl.
    *A61N 5/10*    (2006.01)
(52) U.S. Cl.
    CPC ......... *A61N 5/1031* (2013.01); *A61N 5/1042* (2013.01); *A61N 5/1048* (2013.01); *A61N 2005/1074* (2013.01)
(58) Field of Classification Search
    None
    See application file for complete search history.

(56) References Cited

U.S. PATENT DOCUMENTS

2005/0008121 A1    1/2005    Low et al.
2008/0253516 A1    10/2008   Hui et al.
(Continued)

FOREIGN PATENT DOCUMENTS

CA    2650421 A1    11/2007
CN    1126622 A     7/1996
(Continued)

OTHER PUBLICATIONS

First search report of Chinese Application No. 202010970428.4 issued on Sep. 22, 2023.

*Primary Examiner* — Marcus H Taningco
(74) *Attorney, Agent, or Firm* — Emerson, Thomson & Bennett, LLC; Roger D. Emerson; Seth J. Niemi

(57) ABSTRACT

A method, controller, and system for controlling a radiation dose in radiotherapy of a patient and a computer storage medium are provided. The method includes: irradiating rays to a target area of the patient through a collimator; and keeping, after a source carrier starts to separate from the collimator in a process of controlling separation of the source carrier and the collimator, timing radiation of the rays or calculating the radiation dose of the rays such that the radiation dose of the rays received by the patient is equal to a radiation dose required for the radiotherapy. Therefore, the radiation dose of the rays received by the patient in an entire treatment process may reach the radiation dose actually required during the radiotherapy, thereby improving a radiation dose control accuracy and a treatment effect during the radiotherapy.

20 Claims, 3 Drawing Sheets

Setting a timing start time, and timing radiation of rays, in a process of aligning of a source carrier and a collimator, before the source carrier and the collimator are aligned, and/or, setting a timing end time, and timing the radiation of the rays until the radiation of the rays ends, in a process of controlling separation of the source carrier and the collimator, after the source carrier starts to separate from the collimator —S101

Making a radiation dose of the rays from the start timing time to the end timing time equal to a radiation dose required for the radiotherapy —S102

(56) References Cited

U.S. PATENT DOCUMENTS

| | | |
|---|---|---|
| 2009/0213991 A1 | 8/2009 | Brown et al. |
| 2010/0288916 A1 | 11/2010 | Cho et al. |
| 2011/0319741 A1 | 12/2011 | Brown |
| 2016/0038768 A1 | 2/2016 | Liu |
| 2018/0015307 A1 | 1/2018 | Kumata et al. |
| 2018/0228452 A1 | 8/2018 | Badal-Soler |
| 2018/0318607 A1 | 11/2018 | Wilbur et al. |
| 2019/0255355 A1* | 8/2019 | Nordström ........... A61N 5/1071 |
| 2021/0023395 A1 | 1/2021 | Heese et al. |
| 2021/0038913 A1* | 2/2021 | Liu ..................... A61N 5/1081 |
| 2021/0379406 A1 | 12/2021 | Ni et al. |

FOREIGN PATENT DOCUMENTS

| | | |
|---|---|---|
| CN | 102023308 A | 4/2011 |
| CN | 103961119 A | 8/2014 |
| CN | 104225807 A | 12/2014 |
| CN | 109011217 A | 12/2018 |
| CN | 109011219 A | 12/2018 |
| CN | 209984816 U | 1/2020 |
| CN | 111010868 A | 4/2020 |
| DE | 2937598 A1 | 3/1981 |
| EP | 2617463 A1 | 7/2013 |
| GB | 1309230 A | 3/1973 |
| JP | 2014000210 A | 1/2014 |
| WO | 2009075714 A1 | 6/2009 |
| WO | 2017025067 A1 | 2/2017 |
| WO | 2020029148 A1 | 2/2020 |
| WO | 2020038073 A1 | 2/2020 |
| WO | 2020038220 A1 | 2/2020 |

* cited by examiner

S101 — Setting a timing start time, and timing radiation of rays, in a process of aligning of a source carrier and a collimator, before the source carrier and the collimator are aligned, and/or, setting a timing end time, and timing the radiation of the rays until the radiation of the rays ends, in a process of controlling separation of the source carrier and the collimator, after the source carrier starts to separate from the collimator S102 — Making a radiation dose of the rays from the start timing time to the end timing time equal to a radiation dose required for the radiotherapy

Fig. 1

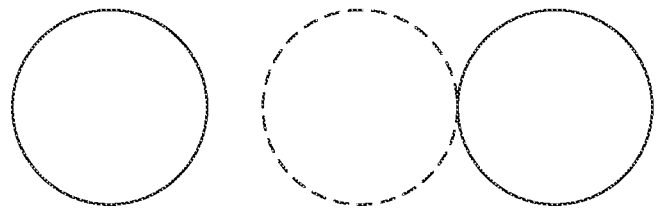
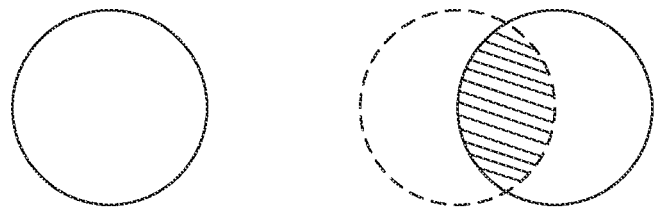

Fig. 2

METHOD, CONTROLLER AND SYSTEM FOR CONTROLLING DOSE IN RADIOTHERAPY

CROSS-REFERENCE TO RELATED APPLICATIONS

The present disclosure is a continuation of U.S. application Ser. No. 17/475,078 filed on Sep. 14, 2021, which claims priority to Chinese application No. 202010970428.4 filed on Sep. 15, 2020, both of which are hereby incorporated by reference in its entirety.

TECHNICAL FIELD

Embodiments of the present disclosure relate to the field of electronic information technology, in particular to a method, controller, and system for controlling a dose in radiotherapy and a computer storage medium.

BACKGROUND

Radiotherapy (RT for short) is one of the important treatment methods for tumors. A radiotherapy system includes a source carrier and a collimator. A radioactive source is placed in the source carrier. The radioactive source may emit radiative rays. The collimator includes a plurality of sets of collimating holes with different apertures, so as to switch for different tumors. A mechanism of radiotherapy is to use various rays (such as protons, neutrons, or heavy ions) to break DNA strands in cell nucleus, so that cells cannot divide and proliferate, achieving a purpose of inhibiting or killing tumors. While killing tumor cells, the radiative rays may also cause certain damage to normal tissues. However, tumor therapy is based on a certain dose of radiation to kill tumor cells, although normal tissues may be damaged, they may still recover. Therefore, the core of radiotherapy lies in setting of the radiation dose.

In the prior art, by rotating the collimator and/or the source carrier, a radiation channel of the source carrier is aligned with or separated from a collimating hole of the collimator, and by setting the radiation channel of the source carrier to be completely aligned with the collimating hole of the collimator, the time taken realizes control of the radiation dose. An entire treatment process is formed from starting of alignment of the collimator with the source carrier to complete separation of the collimator and the source carrier. When the collimator and the source carrier are completely aligned, that is, when the source carrier and the collimator are fully overlapped, a tumor site may receive a preset radiation dose of radiative rays within a preset period.

However, in the process of the alignment of the source carrier and the collimator, that is, when the source carrier and the collimator are not fully overlapped, there is still radiative rays emitted, and in this regard, although the collimator blocks the radiative rays emitted by the source carrier and shields part of the radiative rays, a part of the radiative rays is still irradiated to the tumor site through the collimator. Similarly, in the process of separating the source carrier and the collimator, or in a process of switching the collimation holes multiple times during tumor treatment, there are cases where the source carrier and the collimator are not fully overlapped. As a result, when the source carrier and the collimator are not completely aligned, part of the radiative rays is irradiated to the tumor site through the collimator, thereby affecting an actual radiation dose of radiotherapy. Therefore, it is necessary to provide a method for controlling a dose in radiotherapy to compensate the radiation dose during the alignment and/or separation of the source carrier and the collimator, so as to achieve the radiation dose actually required in the radiotherapy process.

SUMMARY

In view of this, one of the technical problems solved by embodiments of the present disclosure is to provide a method, apparatus, controller, and system for controlling a dose in radiotherapy and a computer storage medium. In a tumor treatment process, a radiation dose used during the alignment and/or separation of a source carrier and a collimator is compensated to achieve a radiation dose actually required in the radiotherapy process.

An embodiment of the present disclosure provides a method for controlling a dose in radiotherapy, and the method includes: setting a timing start time, and timing radiation of rays, in a process of alignment of a source carrier and a collimator, before the source carrier and the collimator are aligned, and/or, setting a timing end time, and timing the radiation of the rays until the radiation of the rays ends, in a process of controlling separation of the source carrier and the collimator, after the source carrier starts to separate from the collimator; and making a radiation dose of the rays from the timing start time to the timing end time equal to a radiation dose required for the radiotherapy.

Exemplarily, in an embodiment of the present disclosure, adjusting a time point at which an overlapping area between the source carrier and the collimator reaches a first preset threshold as the timing start time for the radiation of the rays; and/or adjusting a time point at which an overlapping area between the source carrier and the collimator reaches a second preset threshold as the timing end time for the radiation of the rays.

Exemplarily, in an embodiment of the present disclosure, determining, based on a radiation dose of a first ray corresponding to the overlapping area between the source carrier and the collimator, a radiation dose of rays in a first period from the timing start time to a time point at which the source carrier and the collimator are completely aligned, in the process of alignment of the source carrier and the collimator; and/or determining, based on a radiation dose of a second ray corresponding to the overlapping area between the source carrier and the collimator, a radiation dose of rays in a second period from a time point at which the source carrier starts to separate from the collimator to the timing end time, in the process of controlling the separation of the source carrier and the collimator; and making a sum of the radiation dose of the rays in the first period and/or the radiation dose of the rays in the second period and a radiation dose of rays in a third period during which the source carrier and the collimator are completely aligned is equal to the radiation dose required for the radiotherapy.

Exemplarily, in an embodiment of the present disclosure, in the process of the alignment of the source carrier and the collimator, when the overlapping area between the source carrier and the collimator is A % of a full overlapping area, a radiation dose rate is x1% of a dose rate for the full overlapping area, x1 and A are positive integers; and in the process of controlling the separation of the source carrier and the collimator, when the overlapping area between the source carrier and the collimator is B % of the full overlapping area, a radiation dose rate is y1% of the dose rate for the full overlapping area, and y1 and B are positive integers. The full overlapping area refers to an overlap area between the source carrier and the collimator when a collimating hole of the collimator is in-line with a radiation channel of the source carrier.

Exemplarily, in an embodiment of the present disclosure, a radiation dose rate corresponding to the overlapping area between the source carrier and the collimator which reaches the first preset threshold is x % of a dose rate for the full overlapping area, and x is a positive integer; and a radiation dose rate corresponding the overlapping area between the source carrier and the collimator which reaches the second preset threshold is y % of the dose rate for the full overlapping area, and y is a positive integer.

Exemplarily, in an embodiment of the present disclosure, adjusting the timing start time for the radiation of the rays forward by a first preset period; and adjusting the timing end time for the radiation of the rays backward by a second preset period.

Exemplarily, in an embodiment of the present disclosure, receiving a radiotherapy plan and performing radiotherapy according to an irradiation modality set in the radiotherapy plan.

Exemplarily, in an embodiment of the present disclosure, the irradiation modality includes performing radiotherapy using a plurality of different collimators, and timing radiation of rays, in the process of the alignment of the source carrier and at least one collimator, before the source carrier and the collimator are aligned; and/or, timing the radiation of the rays until the radiation of the rays ends, in the process of controlling the separation of the source carrier and at least one collimator, after the source carrier starts to separate from the collimator.

An embodiment of the present disclosure provides an apparatus for controlling a dose, the apparatus for controlling a dose includes a time determination module and a setting module. The time determination module is configured to set a timing start time, and time radiation of rays, in the process of the alignment of a source carrier and a collimator, before the source carrier and the collimator are aligned, and/or, set a timing end time, and time the radiation of the rays until the radiation of the rays ends, in a process of controlling separation of the source carrier and the collimator, after the source carrier starts to separate from the collimator. The setting module is configured to make a radiation dose of the rays from the timing start time to the timing end time equal to a radiation dose required for the radiotherapy.

An embodiment of the present disclosure provides a controller, including: a processor and a memory, a computer program being stored on the memory. The processor is configured to execute the computer program stored on the memory to implement: the method for controlling a dose as described in the first aspect or any one of the embodiments of the first aspect.

An embodiment of the present disclosure provides a system for controlling a dose in radiotherapy. The system for controlling a dose includes: a master device, a slave device, a timer, at least one drive, and at least one motor.

An embodiment of the present disclosure provides a method for controlling a dose in radiotherapy of a patient, comprising: irradiating rays to a target area of the patient through a collimator; keeping, after a source carrier starts to separate from the collimator in a process of controlling separation of the source carrier and the collimator, timing the radiation of the rays or calculating radiation dose of the rays, such that the radiation dose of the rays received by the patient is equal to a radiation dose required for the radiotherapy.

Exemplarily, in an embodiment of the present disclosure, keeping, after the source carrier starts to separate from the collimator in the process of controlling separation of the source carrier and the collimator, timing the radiation of the rays or calculating radiation dose of the rays till a preset duration is reached after the source carrier starts to separate from the collimator.

Exemplarily, in an embodiment of the present disclosure, keeping, after the source carrier starts to separate from the collimator in the process of controlling separation of the source carrier and the collimator, timing the radiation of the rays or calculating radiation dose of the rays till an overlapping area between the source carrier and the collimator is equal to or less than a second preset threshold.

Exemplarily, in an embodiment of the present disclosure, starting to time the radiation of the rays before the source carrier is aligned with the collimator in the process of alignment of the source carrier and the collimator and ending timing the radiation of the rays till a preset duration is reached after the source carrier starts to separate from the collimator in the process of controlling separation of the source carrier and the collimator such that the radiation dose of the rays received by the patient is equal to the radiation dose required for the radiotherapy; or starting to calculate the radiation dose of the rays before the source carrier is aligned with the collimator in the process of alignment of the source carrier and the collimator and ending calculating the radiation dose of the rays till a preset duration is reached after the source carrier starts to separate from the collimator in the process of controlling separation of the source carrier and the collimator such that the radiation dose of the rays received by the patient is equal to the radiation dose required for the radiotherapy.

Exemplarily, in an embodiment of the present disclosure, starting to time the radiation of the rays before the source carrier is aligned with the collimator in the process of alignment of the source carrier and the collimator and ending timing the radiation of the rays when an overlapping area between the source carrier and the collimator reaches a second preset threshold in the process of controlling separation of the source carrier and the collimator such that the radiation dose of the rays received by the patient is equal to the radiation dose required for the radiotherapy; or starting to calculate the radiation dose of the rays before the source carrier is aligned with the collimator in the process of alignment of the source carrier and the collimator and ending calculating the radiation dose of the rays when an overlapping area between the source carrier and the collimator reaches a second preset threshold such that the radiation dose of the rays received by the patient is equal to the radiation dose required for the radiotherapy.

The master device and the slave device are in communication connection. The master device includes an image user interface, and the master device receives a user operation command and sends the user operation command to the slave device.

The slave device includes at least one controller as described in the third aspect, and the controller sends a control instruction to the at least one drive according to the user operation command.

The drive is connected to the motor. The drive sends the control instruction to the motor, and the motor drives a source carrier and/or a collimator to move according to the control instruction, so that a radiation channel in the source carrier is aligned with or separated from a collimating hole in the collimator.

The slave device further includes the timer. The timer receives movement position information of the source carrier and/or the collimator, and sends the control instruction to the drive based on the movement position information.

Exemplarily, in an embodiment of the present disclosure, the system for controlling a dose further includes at least one encoder, the encoder is electrically connected to the motor, the encoder feeds back the movement position information of the source carrier and/or the collimator to the drive and the slave device; and the timer receives the movement position information sent by the encoder.

In a fifth aspect, an embodiment of the present disclosure provides a computer storage medium, the computer storage medium storing a computer program, the computer program, when executed by a processor, implements the method for controlling a dose as described in the first aspect or any one of the embodiments of the first aspect.

In a sixth aspect, an embodiment of the present disclosure provides a method for controlling a dose in radiotherapy of a patient. The method includes: starting to time radiation of rays or calculate radiation dose of the rays before a source carrier is aligned with a collimator in a process of alignment of the source carrier and the collimator; irradiating rays to a target area of the patient through the collimator till the radiation dose of the rays received by the patient is equal to a radiation dose required for the radiotherapy.

In a seventh aspect, an embodiment of the present disclosure provides a controller. The controller includes a processor and a memory. A computer program is stored on the memory. The processor is configured to execute the computer program stored on the memory to implement: starting to time the radiation of the rays before the source carrier is aligned with the collimator in the process of alignment of the source carrier and the collimator till a radiation dose of the rays received by the patient is equal to a radiation dose required for the radiotherapy.

In a eighth aspect, an embodiment of the present disclosure provides a system for controlling a dose in radiotherapy of a patient. The system comprises: a master device, a slave device, at least one drive, and at least one motor. The master device and the slave device are in communication connection. The master device comprises a user interface, and the master device receives a user operation command and sends the user operation command to the slave device. The slave device comprises at least one controller according to the sixth aspect, and the controller sends a control instruction to the at least one drive according to the user operation command. The drive is connected to the motor. The drive sends the control instruction to the motor, and the motor drives a source carrier and/or a collimator to move according to the control instructions, so that a radiation channel in the source carrier is aligned with or separated from a collimating hole in the collimator The embodiments of the present disclosure provide a method, controller, and system for controlling a dose in radiotherapy and a computer storage medium. The method for controlling a dose includes: setting a timing start time, and timing radiation of rays, in the process of alignment of a source carrier and a collimator, before the source carrier and the collimator are aligned, the timing start time being earlier than the time point at which the collimator and the source carrier are completely aligned, and/or, setting a timing end time, and timing the radiation of the rays until the radiation of the rays ends, in a process of controlling separation of the source carrier and the collimator, after the source carrier starts to separate from the collimator, the timing end time being later than the time point at which the collimator starts to separate from the source carrier; and making a radiation dose of the rays from the timing start time to the timing end time equal to a radiation dose required for the radiotherapy. Therefore, the radiation dose received by the collimator and the source carrier in an entire treatment process may reach the radiation dose actually required during the radiotherapy, thereby improving a radiation dose control accuracy and a treatment effect during the radiotherapy.

BRIEF DESCRIPTION OF THE DRAWINGS

Hereinafter, some specific embodiments of the embodiments of the present disclosure will be described in detail in an exemplary but not restrictive method with reference to the accompanying drawings. The same reference numerals in the accompanying drawings indicate the same or similar components or parts. Those skilled in the art should appreciate that these accompanying drawings are not necessarily drawn to scale. In the accompanying drawings:

FIG. 1 is a flowchart of a method for controlling a dose in radiotherapy provided by an embodiment of the present disclosure;

FIG. 2 is a schematic diagram of an alignment process of a source carrier and a collimator provided by an embodiment of the present disclosure;

DETAILED DESCRIPTION OF EMBODIMENTS

Figure 3:
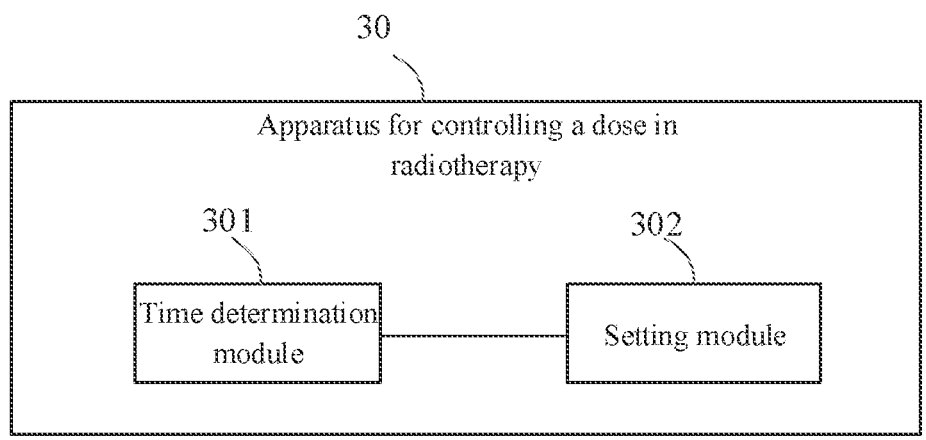
FIG. 3 is a schematic diagram of an apparatus for controlling a dose in radiotherapy provided by an embodiment of the present disclosure.

It should be noted that the first and second in embodiments of the present disclosure are only for distinguishing names, and do not represent a sequence relationship, and cannot be understood as indicating or implying relative importance or implicitly indicating the number of indicated technical features, for example, a first preset threshold and a second preset threshold.

A specific implementation of the embodiments of the present disclosure will be further described below in conjunction with the accompanying drawings of the embodiments of the present disclosure.

Embodiment 1

Embodiment 1 of the present disclosure provides a method for controlling a dose in radiotherapy. FIG. 1 is a flowchart of a method for controlling a dose in radiotherapy provided by an embodiment of the present disclosure. As shown in FIG. 1, the method for controlling a dose includes the following steps:

Step 101, setting a timing start time, and timing radiation of rays, in the process of alignment of a source carrier and a collimator, before the source carrier and the collimator are aligned, and/or, setting a timing end time, and timing the radiation of the rays until the radiation of the rays ends, in a process of controlling separation of the source carrier and the collimator, after the source carrier starts to separate from the collimator.

Here, it should be noted that the method for controlling a dose in radiotherapy provided by the present disclosure is applied to radiotherapy equipment. The radiotherapy equipment includes a source carrier and a collimator. The source carrier is provided with a ray channel outlet corresponding to a radiation source. A plurality of collimating holes are distributed on the collimator, and when the ray channel outlet is aligned with a collimating hole, radiative ray can pass through the ray channel outlet and irradiate a tumor site through the collimating hole. In the process of alignment of the source carrier and the collimator, an overlapping relationship between the source carrier and the collimator may have the following three situations: in a first case, the source carrier and the collimator start to align, in this regard, the source carrier and the collimator are not overlapped at all; in a second case, the source carrier and the collimator are not fully overlapped, that is, partially overlapped; and in a third case, the source carrier and the collimator are completely aligned, and the source carrier and the collimator are fully overlapped. As shown in FIG. 2, FIG. 2 is a schematic diagram of the alignment process of a source carrier and a collimator provided by an embodiment of the present disclosure. In FIG. 2, the source carrier is approaching the collimator as an example for illustration. It may be understood that the collimator may also approach the source carrier in the process of alignment of the source carrier with the collimator, or the source carrier and the collimator approach each other, which is not limited in the embodiments of the present disclosure. In addition, in FIG. 2, two circles with equal diameters respectively represent the ray channel outlet of the source carrier and the collimating hole of the collimator. It may be understood that the ray channel outlet of the source carrier and the collimating hole of the collimator may also be two circles with unequal diameters, which is not limited in the embodiments of the present disclosure. The source carrier and the collimator start to align, and the two circles are tangent. In this regard, the source carrier and the collimator are not overlapped at all, the collimating hole completely shields the radiative rays emitted by the source carrier, and the radiative rays cannot reach the tumor site; the two circles intersect, the source carrier and the collimator are not fully overlapped, that is, partially overlapped, the collimating hole partially shields the radiative rays emitted by the source carrier, and the rays may be irradiated to the tumor site through a partially overlapping area; the source carrier and the collimator are completely aligned, the two circles coincide, the source carrier and the collimator are fully overlapped, and the radiative rays may be completely irradiated to the tumor site through the collimating hole. It should be noted that FIG. 2 uses the alignment process of the source carrier and the collimator as an example for illustration. A separation process of the source carrier and the collimator is opposite to the alignment process. In the separation process, the overlapping relationship between the source carrier and the collimator is the same as the alignment process, and detailed description thereof will be omitted. For example, time to start early and/or end late may be a set fixed value, for example, start early and/or end late of 0.2 s.

Step 102, making a radiation dose of the rays from the timing start time to the timing end time equal to a radiation dose required for the radiotherapy.

During the entire radiotherapy, a radiation dose used in any treatment process is not only related to the diameter of the collimating hole, but also related to time of receiving the rays, and the time of receiving the rays is a period that has been set by a doctor or staff before determining the treatment process. Start timing to end timing constitute the set period. During the entire treatment from start of alignment to the complete separation of the source carrier and the collimator, the source carrier emits radiative rays. The implementation of the present disclosure makes the radiation dose of the rays from the timing start time to the timing end time equal to the radiation dose required for the radiotherapy. The timing start time and/or the timing end time for the radiation of the rays realizes compensation of the radiation dose of the rays. Here are three examples for description.

In a first example, in the process of alignment of the source carrier and the collimator, set the start timing time for the radiation of the rays, and the timing start time is earlier than a time point at which the collimator and the source carrier are completely aligned, in order to time the radiation of the rays in advance, compared with starting timing when the collimator and the source carrier are completely aligned, and ending timing when the separation starts, there is one more first compensation period. A starting point of the first compensation period is a time point corresponding to the start of timing, and an end point of the first compensation period is a time point corresponding to the complete alignment of the source carrier and the collimator. A radiation dose received in the first compensation period is used to compensate the radiation dose actually required. In the first example, the timing start time for the radiation of the rays is adjusted forward by a first preset period. The first preset period is before the collimator and the source carrier are completely aligned. The first compensation period is used as an example for description above, and detailed description thereof will be omitted. The radiation dose actually required may be compensated within the first preset period, thereby improving a radiation dose control accuracy and a treatment effect during the radiotherapy.

In a second example, in the process of controlling the separation of the source carrier and the collimator, set the timing end time for the radiation of the rays, and the timing end time is later than time point at which the collimator starts to separate from the source carrier, compared with starting timing when the collimator and the source carrier are completely aligned, and ending timing when the separation starts, there is one more second compensation period. A starting point of the second compensation period is a time point corresponding to the starting to separate of the source carrier and the collimator, and an end point of the second compensation period is a time point corresponding to the end of timing. A radiation dose received in the second compensation period is used to compensate the radiation dose actually required. In the second example, the timing end time for the radiation of the rays is adjusted backward by a second preset period. The second preset period is after the collimator starts to separate from the source carrier. The second compensation period is used as an example for description above, and detailed description thereof will be omitted. The radiation dose actually required may be compensated within the second preset period, thereby improving a radiation dose control accuracy and a treatment effect during the radiotherapy.

In a third example, in the process of controlling the alignment to separation of the source carrier and the collimator, set the timing start time and the timing end time for the radiation of the rays, compared with starting timing when the collimator and the source carrier are completely aligned, and ending timing when the separation starts, a third compensation period and a fourth compensation period are added. The third compensation period is the same as the first compensation period in the first example, and detailed description thereof will be omitted. The fourth compensation period is the same as the second compensation period in the second example, and detailed description thereof will be omitted. Radiation doses received in the third compensation period and the fourth compensation period are used to compensate the radiation dose actually required, thereby improving a radiation dose control accuracy and a treatment effect during the radiotherapy.

It should be noted that the first and second in the embodiments of the present disclosure are only for distinguishing names, and do not represent a sequence relationship, and cannot be understood as indicating or implying relative importance or implicitly indicating the number of indicated technical features, for example, the first compensation period, the second compensation period, the third compensation period, and the fourth compensation period, where the first compensation period and the second compensation period may be equal or unequal, which is not limited in the embodiments of the present disclosure.

Exemplarily, in an embodiment of the present disclosure, after setting the timing start time and the timing end time in the embodiment of the present disclosure, a radiotherapy plan may be received and radiotherapy is performed according to an irradiation modality set in the radiotherapy plan.

Since the timing start time and the timing end time are set in the present disclosure, after receiving the radiotherapy plan and performing radiotherapy according to the irradiation modality set in the radiotherapy plan, so that the radiation dose received by the collimator and the source carrier in the entire treatment process may reach the radiation dose actually required during the radiotherapy, the radiation dose control accuracy and the treatment effect during the radiotherapy are improved.

Exemplarily, the irradiation modality in the present disclosure includes performing radiotherapy using a plurality of different collimators, in the process of alignment of the source carrier and at least one collimator, before the source carrier and the collimator are aligned, timing radiation time of rays in advance; and/or, in a process of controlling separation of the source carrier and at least one collimator, after the source carrier starts to separate from the collimator, delay timing the radiation of the rays until the radiation of the rays ends.

The method for controlling a dose in radiotherapy provided in the present disclosure is applied to radiotherapy equipment. The radiotherapy equipment includes a source carrier and a collimator. The number of collimators may be one or more. In actual application, the source carrier may be controlled to achieve alignment with at least one collimator according to a specific situation. In the process of aligning of the source carrier and the collimator, before the source carrier and the collimator are aligned, the timing start time may be set, and radiation of rays is timed; or, in the process of controlling the separation of the source carrier and the collimator, after the source carrier starts to separate from the collimator, the timing end time may be set, and the radiation of the rays is timed until the radiation of the rays ends; or in the process from the alignment to the separation of the source carrier and the collimator, the timing start time and the timing end time may be set. The specific implementation is consistent with steps 101-102, and detailed description thereof will be omitted.

Embodiment 2

Exemplarily, the setting a timing start time, in an embodiment of the present disclosure, adjusting a time point at which an overlapping area between the source carrier and the collimator reaches a first preset threshold as the timing start time for the radiation of the rays.

In the radiotherapy equipment, the collimator may be attached to a surface of the source carrier, or it may also be set at a certain distance from the source carrier, which is not limited in the embodiments of the present disclosure, as long as the collimator can move relative to the source carrier, or the source carrier can move relative to the collimator, or the collimator and the source carrier can move relative to each other, so that the collimator and the source carrier are aligned or separated. The overlapping area between the source carrier and the collimator may be a relative overlap area of the source carrier and the collimator, for example, the source carrier is projected onto the collimator, or the collimator is projected onto the source carrier, so as to calculate the overlap area between the source carrier and the collimator. In the process of alignment of the source carrier and the collimator, in the present disclosure, the time point at which the overlapping area between the source carrier and the collimator reaches the first preset threshold is adjusted as the timing start time for the radiation of the rays.

It should be noted that at least one collimating hole with different apertures is distributed on the collimator, and the first preset thresholds for collimating holes of different apertures are different. For example, the aperture of collimating hole 1 is smaller than that of collimating hole 2. Because the aperture of the collimating hole 1 is small, in the process of alignment or separation of the collimator and the source carrier, even in the case of complete alignment, the radiation dose received by a tumor site is very limited, therefore, a radiation dose that the collimating hole 1 needs to compensate is more than that of the collimating hole 2. Setting the first preset threshold corresponding to the collimating hole 1 to be larger than the first preset threshold corresponding to the collimating hole 2, so that the timing start time of the collimating hole 1 is later than that of the collimating hole 2, so that the more the radiation dose received by the collimating hole 1, the radiation dose control accuracy and the treatment effect during the radiotherapy are improved.

Exemplarily, in an embodiment of the present disclosure, determining a radiation dose of rays in a first period from the timing start time to complete the alignment of the source carrier and the collimator, based on a radiation dose of a first ray corresponding to the overlapping area between the source carrier and the collimator, in the process of controlling the alignment of the source carrier and the collimator.

A relationship between the overlapping area and the radiation dose in the present disclosure is a positive correlation, that is, the larger the overlapping area between the collimator and the source carrier, the more the radiation dose received, and the smaller the overlapping area between the collimator and the source carrier, the smaller the radiation dose received. In the process of alignment of the source carrier and the collimator, the embodiment of the present disclosure determines the radiation dose of the rays in the first period from the timing start time to the complete alignment of the source carrier and the collimator, based on the radiation dose of the first ray corresponding to the overlapping area between the source carrier and the collimator.

Exemplarily, in an embodiment of the present disclosure, a radiation dose rate corresponding to the overlapping area between the source carrier and the collimator which reaches the first preset threshold, is x % of a dose rate for the full overlapping area, and x is a positive integer. The x % of the dose rate for the full overlapping area indicates that the radiation dose rate is equal to a dose rate for the full overlapping area multiplied by x %. The first preset threshold may be determined based on a dose rate for a relative overlapping area between the source carrier and the collimator. For example, it is set when the radiation dose rate is x % of the dose rate for the full overlapping area, the overlapping area between the source carrier and the collimator reaches the first preset threshold. In the embodiments of the present disclosure, in the process of alignment of the source carrier and the collimator, a corresponding relationship between the overlapping area and the radiation dose rate is set. In an actual situation, the first preset threshold may be determined by the radiation dose rate. The time point at which the overlapping area between the source carrier and the collimator reaches the first preset threshold is adjusted as the timing start time for the radiation of the rays. In the present disclosure, the timing start time is earlier than the time point at which the collimator and the source carrier are completely aligned. The timing start time to a time point at which the collimator and the source carrier are completely aligned constitute the first period. The radiation dose received in the first period is used to compensate the radiation dose actually required. In the process of controlling the alignment of the source carrier and the collimator, the radiation dose of the rays in the first period accumulates a radiation dose of rays in the third period during which the source carrier and the collimator are completely aligned (i.e., a sum of the radiation dose of the rays in the first period and the radiation dose of the rays in the third period during which the source carrier and the collimator are completely aligned) is the radiation dose required for the radiotherapy, thereby improving the radiation dose control accuracy and the treatment effect during the radiotherapy.

Embodiment 3

Exemplarily, the setting a timing end time, in an embodiment of the present disclosure, comprises: adjusting a time point at which an overlapping area between the source carrier and the collimator reaches a second preset threshold as the timing end time for the radiation of the rays.

The separation and alignment of the source carrier and the collimator are two opposite processes. The embodiment of the present disclosure can not only start timing earlier in the alignment process of the source carrier and the collimator, that is, the timing start time is earlier than the time point at which the source carrier and the collimator are completely aligned, so as to realize the compensation to the radiation dose of the rays; but also end the timing later in the process of separating the source carrier and the collimator, that is, the timing end time is later than the time point at which the source carrier starts to separate from the collimator, so as to realize the compensation to the radiation dose of the rays. In the present disclosure, the time point at which the overlapping area between the source carrier and the collimator reaches the second preset threshold is adjusted as the timing end time for the radiation of the rays.

It should be noted that the second preset thresholds for collimating holes of different apertures are different. For example, the aperture of collimating hole 1 is smaller than that of collimating hole 2, in the process of separating the collimator and the source carrier, setting the preset threshold corresponding to the collimating hole 1 to be larger than the preset threshold corresponding to the collimating hole 2, so that the timing end time of the collimating hole 1 is earlier than that of the collimating hole 2, so that the more the radiation dose received by the collimating hole 1, the radiation dose control accuracy and the treatment effect during the radiotherapy are improved.

Exemplarily, in an embodiment of the present disclosure, determining a radiation dose of rays in a second period from a time point at which the source carrier starts to separate from the collimator to the timing end time, based on a radiation dose of a second ray corresponding to the overlapping area between the source carrier and the collimator, in the process of controlling the separation of the source carrier and the collimator.

A relationship between the overlapping area and the radiation dose in the present disclosure is a positive correlation. In the process of controlling the separation of the source carrier and the collimator, the embodiment of the present disclosure determines the radiation dose of the rays in the second period from the source carrier and the collimator starting to separate to the timing end time, based on the radiation dose of the second ray corresponding to the overlapping area between the source carrier and the collimator.

Exemplarily, in an embodiment of the present disclosure, a radiation dose rate corresponding to the overlapping area between the source carrier and the collimator which reaches the second preset threshold is y % of the dose rate for the full overlapping area, and y is a positive integer. The y % of the dose rate for the full overlapping area indicates that the radiation dose rate is equal to a dose rate for the full overlapping area multiplied by y %. The second preset threshold may be determined based on a dose rate for a relative overlapping area between the source carrier and the collimator. For example, it is set when the radiation dose rate is y % of the dose rate for the full overlapping area, the overlapping area between the source carrier and the collimator reaches the second preset threshold. In the embodiments of the present disclosure, in the process of controlling the separation of the source carrier and the collimator, a corresponding relationship between the overlapping area and the radiation dose rate is set. In an actual situation, the second preset threshold may be determined by the radiation dose rate. The time point at which the overlapping area between the source carrier and the collimator reaches the second preset threshold is adjusted as the timing end time for the radiation of the rays. The timing end time is later than the time point at which the collimator starts to separate from the source carrier. The time point at which the collimator starts to separate from the source carrier to the timing end time constitute the second period. The radiation dose received in the second period is used to compensate the radiation dose actually required. In the process of controlling the separation of the source carrier and the collimator, the radiation dose of the rays in the second period accumulates a radiation dose of rays in the third period during which the source carrier and the collimator are completely aligned, is the radiation dose required for the radiotherapy, thereby improving the radiation dose control accuracy and the treatment effect during the radiotherapy.

Embodiment 4

It should be noted that in Embodiment 2, in the process of controlling the alignment of the source carrier and the collimator, the radiation dose of the rays is compensated, and in Embodiment 3, in the process of controlling the separation of the source carrier and the collimator, the radiation dose of the rays is compensated. Embodiment 2 and Embodiment 3 are two opposite processes. Embodiment 4 of the present disclosure combines Embodiment 2 and Embodiment 3. In an entire treatment process of controlling the source carrier and the collimator to get aligned and then separated, the radiation dose of the rays is compensated.

Exemplarily, in the process of controlling the alignment of the source carrier and the collimator, when the overlapping area between the source carrier and the collimator is A % of a full overlapping area, a radiation dose rate is x1% of a dose rate for the full overlapping area, x1 and A are positive integers; and in the process of controlling the separation of the source carrier and the collimator, when the overlapping area between the source carrier and the collimator is B % of the full overlapping area, a radiation dose rate is y1% of the dose rate for the full overlapping area, and y1 and B are positive integers. x1%+y1%=100%.

The radiation dose rate refers to a radiation dose per unit time. The full overlapping area is used to indicate an overlapping area when the source carrier and the collimator are completely aligned. A dose rate for the full overlapping area is set to 100%. A % of the full overlapping area indicates that the overlapping area is equal to the full overlapping area multiplied by A %, x1% of the dose rate for the full overlapping area indicates that the radiation dose rate is equal to a dose rate for the full overlapping area multiplied by x1%, B % for the full overlapping area indicates that the overlapping area is equal to the full overlapping area multiplied by B %, and y1% of the dose rate for the full overlapping area indicates that the radiation dose rate is equal to a dose rate for the full overlapping area multiplied by y1%. In the embodiments of the present disclosure, a relationship between the radiation dose rate and an overlapping rate is a positive correlation, that is, the higher the overlapping rate, the higher the radiation dose rate. In the process of alignment of the source carrier and the collimator, when the overlapping area between the source carrier and the collimator is A % of the full overlapping area, the radiation dose rate is x1% of the dose rate for the full overlapping area, and, in the process of controlling the separation of the source carrier and the collimator, when the overlapping area between the source carrier and the collimator is B % of the full overlapping area, the radiation dose rate is y1% of the dose rate for the full overlapping area, and x1%+y1%=100% in Embodiment 4 of the present disclosure, that is, the x1% of the dose rate for the full overlapping area is added to the y1% of the dose rate for the full overlapping area, which is equal to the dose rate for the full overlapping area. A plurality of combinations of different overlapping rates may be obtained, and different combinations of overlapping rates correspondingly determine different timing start times and timing end times. Based on the timing start time and the timing end time, the radiation dose of the rays is compensated, thereby improving the radiation dose control accuracy and the treatment effect during the radiotherapy.

It should be noted that in the process of controlling the source carrier and the collimator to get aligned or separated, if the source carrier is controlled to move relative to the collimator to achieve alignment or separation, the overlapping area between the source carrier and the collimator is determined based on position information of the source carrier; if the collimator is controlled to move relative to the source carrier to achieve alignment or separation, the overlapping area between the source carrier and the collimator is determined based on position information of the collimator; or if a relative movement of the collimator and the source carrier is controlled to achieve alignment or separation, the overlapping area between the source carrier and the collimator is determined based on position information of the source carrier and the collimator, which is not limited in the embodiments of the present disclosure.

When the overlapping area between the source carrier and the collimator is A % of the full overlapping area, it is determined as the timing start time for the radiation of the rays. The timing start time is earlier than the time point at which the collimator and the source carrier are completely aligned. The timing start time to a time point at which the collimator and the source carrier are completely aligned constitute the first period. When the overlapping area between the source carrier and the collimator is B % of the full overlapping area, it is determined as the timing end time for the radiation of the rays. The timing end time is later than the time point at which the collimator starts to separate from the source carrier. The time point at which the collimator starts to separate from the source carrier to the timing end time constitute the second period. The period during which the source carrier and the collimator are completed aligned is regarded as the third period. The first period and the second period are radiation dose compensation periods, and the radiation doses received in the first period and the second period are used to compensate the radiation dose actually required. The radiation dose of the rays in the first period, the radiation dose of the rays in the second period, and the radiation dose of the rays in the third period during which the source carrier and the collimator are completely aligned, are accumulated to obtain the radiation dose required for the radiotherapy, thereby improving the radiation dose control accuracy and the treatment effect during the radiotherapy.

Embodiment 5

An embodiment of the present disclosure provides an apparatus for controlling a dose in radiotherapy, as shown in FIG. 3, FIG. 3 is an apparatus for controlling a dose in radiotherapy provided by an embodiment of the present disclosure. The apparatus for controlling a dose 30 includes a time determination module 301 and a setting module 302.

The time determination module 301 is configured to set a timing start time, and time radiation of rays, in a process of alignment of a source carrier and a collimator, before the source carrier and the collimator are aligned, and/or, set a timing end time, and time the radiation of the rays until the radiation of the rays ends, in a process of controlling separation of the source carrier and the collimator, after the source carrier starts to separate from the collimator.

The setting module 302 is configured to make a radiation dose of the rays from the timing start time to the timing end time equal to a radiation dose required for the radiotherapy.

Exemplarily, in an embodiment of the present disclosure, the time determination module 301 is further configured to adjust a time point at which an overlapping area between the source carrier and the collimator reaches a first preset threshold as the timing start time for the radiation of the rays; and/or adjust a time point at which an overlapping area between the source carrier and the collimator reaches a second preset threshold as the timing end time for the radiation of the rays.

Exemplarily, in an embodiment of the present disclosure, the setting module 302 is further configured to determine a radiation dose of rays in a first period from the timing start time to a time point at which the source carrier and the collimator is completely aligned, based on a radiation dose of a first ray corresponding to the overlapping area between the source carrier and the collimator, in the process of controlling the source carrier and the collimator to be aligned; and/or determine a radiation dose of rays in a second period from a time point at which the source carrier starts to separate from the collimator to the timing end time, based on a radiation dose of a second ray corresponding to the overlapping area between the source carrier and the collimator, in the process of controlling the separation of the source carrier and the collimator; and make a sum of the radiation dose of the rays in the first period and/or the radiation dose of the rays in the second period and a radiation dose of rays in a third period during which the source carrier and the collimator are completely aligned equal to the radiation dose required for the radiotherapy.

Exemplarily, in an embodiment of the present disclosure, the setting module 302 is further configured to, in the process of controlling the alignment of the source carrier and the collimator, when the overlapping area between the source carrier and the collimator is A % of a full overlapping area, a radiation dose rate is x1% of a dose rate for the full overlapping area, x1 and A are positive integers; and in the process of controlling the separation of the source carrier and the collimator, when the overlapping area between the source carrier and the collimator is B % of the full overlapping area, a radiation dose rate is y1% of the dose rate for the full overlapping area, and y1 and B are positive integers.

Exemplarily, in an embodiment of the present disclosure, the setting module 302 is further configured to, a radiation dose rate corresponding to the overlapping area between the source carrier and the collimator which reaches the first preset threshold is x % of a dose rate for the full overlapping area, and x is a positive integer; and a radiation dose rate corresponding to the overlapping area between the source carrier and the collimator which reaches the second preset threshold is y % of the dose rate for the full overlapping area, and y is a positive integer.

Exemplarily, in an embodiment of the present disclosure, the time determination module 301 is further configured to adjust the timing start time for the radiation of the rays forward by a first preset period; and adjust the timing end time for the radiation of the rays backward by a second preset period.

Exemplarily, in an embodiment of the present disclosure, the apparatus for controlling a dose 30 further comprises a receiving module, and the receiving module is further configured to receive a radiotherapy plan and perform radiotherapy according to an irradiation modality set in the radiotherapy plan.

Exemplarily, in an embodiment of the present disclosure, the irradiation modality includes performing radiotherapy using a plurality of different collimators, and the time determination module 301 is further configured to time radiation of rays, in a process of alignment of the source carrier and at least one collimator, before the source carrier and the collimator are aligned; and/or, time the radiation of the rays until the radiation of the rays ends, in a process of controlling separation of the source carrier and at least one collimator, after the source carrier starts to separate from the collimator.

Embodiment 6

Figure 4:
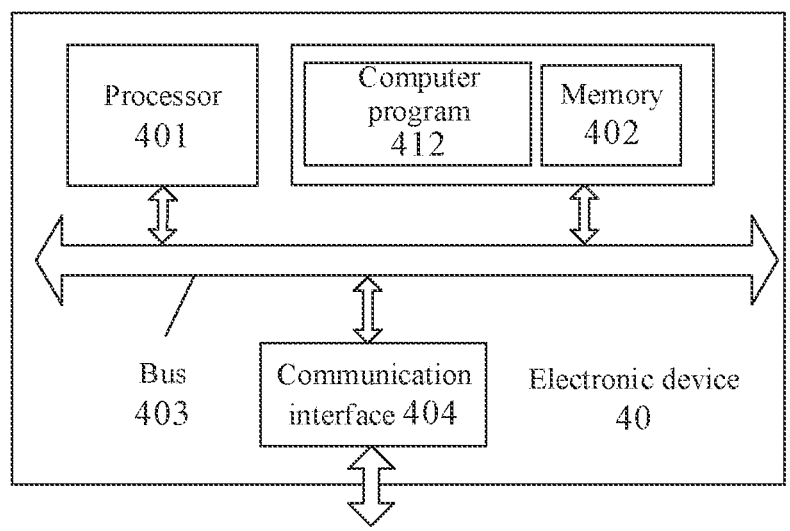
FIG. 4 is a structural diagram of a controller provided by an embodiment of the present disclosure.

Based on the method for controlling a dose in radiotherapy described in Embodiment 1 to Embodiment 4 above, an embodiment of the present disclosure provides a controller, as shown in FIG. 4, FIG. 4 is a structural diagram of a controller provided by an embodiment of the present disclosure, the controller 40 includes: at least one processor 401; a memory 402, the memory stores at least one program 412, the processor 401 and the memory 402 are electrically connected, the at least one program, when executed by the at least one processor 401, cause the at least one processor 401 to implement the method for controlling a dose as described in Embodiment 1 to Embodiment 4.

Exemplarily, in an embodiment of the present disclosure, the controller 40 further includes: a bus 403 and a communication interface 404, and the at least one processor 401, the memory 402, and the communication interface 404 communicate with each other through the bus 403.

Embodiment 7

Figure 5:
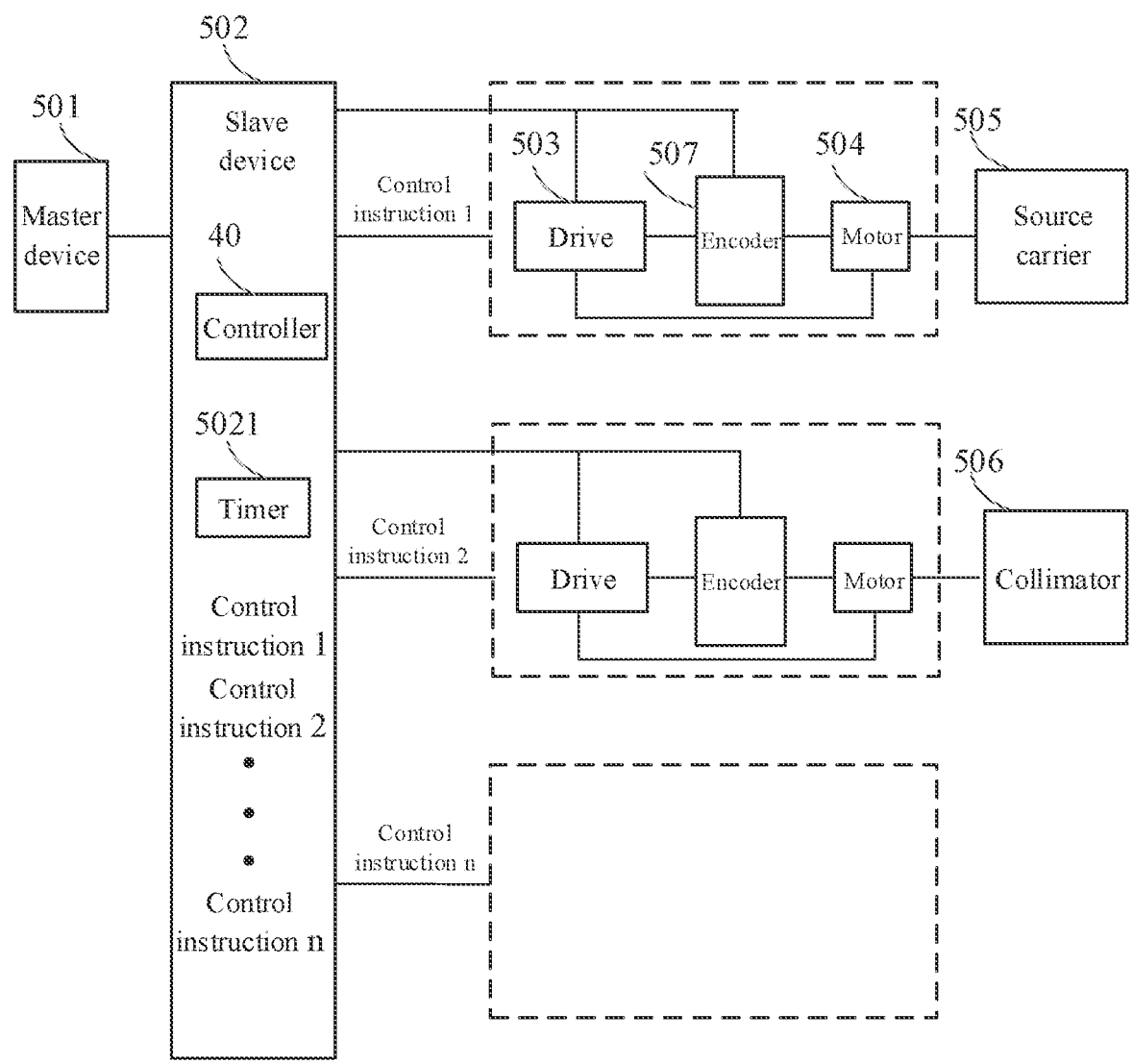
FIG. 5 is a system for controlling a dose in radiotherapy provided by an embodiment of the present disclosure.

An embodiment of the present disclosure provides a system for controlling a dose in radiotherapy, as shown in FIG. 5, FIG. 5 is a system for controlling a dose in radiotherapy provided by an embodiment of the present disclosure. The system for controlling a dose includes: a master device 501, a slave device 502, at least one drive 503, and at least one motor 504;

The master device 501 and the slave device 502 are in communication connection, the master device 501 includes an image user interface, and the master device 501 receives a user operation command and sends the user operation command to the slave device 502.

The slave device 502 includes at least one controller 40 in Embodiment 6. The controller 40 sends a control instruction to the at least one drive 503 according to the user operation command. Of course, the slave device 502 may also send the control instruction to the at least one drive 503. In FIG. 5, the slave device may send n control instructions, which are shown as control instruction 1, control instruction 2, . . . control instruction n. When n control instructions are sent, they may be sent at the same time or separately, which is not limited in the embodiments of the present disclosure. Here, the slave device 502 sends the control instruction 1 to the drive 503 of a source carrier 505, and the slave device 502 sends the control instruction 2 to the drive of a collimator 506. It may be understood that the slave device 502 may also send control instructions to other devices. In FIG. 5, only sending the control instruction 1 and the control instruction 2 is shown, but it does not mean that the embodiments of the present disclosure are limited thereto.

The drive 503 is connected to the motor 504, the drive 503 sends the control instruction to the motor 504, the motor 504 drives the source carrier 505 and/or the collimator 506 to move according to the control instruction, so that a radiation channel in the source carrier 505 aligns with or separates from a collimating hole in the collimator 506.

The slave device 502 further includes a timer 5021, the timer 5021 receives movement position information of the source carrier 505 and/or the collimator 506, and sends the control instruction to the drive 503 based on the movement position information. In an embodiment of the present disclosure, the control instruction may be a movement instruction, that is, the controller 40 sends a movement instruction to the drive 503 according to the user operation command, or the timer 5021 sends a movement instruction to the drive 503 based on the movement position information. After receiving the movement instruction, the drive 503 sends the movement instruction to the motor 504. The motor 504 drives the source carrier 505 and/or the collimator 506 to move according to the movement instruction, so that a radiation channel in the source carrier 505 is aligned with or separated from a collimating hole in the collimator 506.

It should be noted that the master device 501 may be a computer device with a user interface that may receive the operation command from a user. The slave device 502 is a computer device that directly controls the device (such as the drive 503 in FIG. 5) and acquires a status of the device. The operation command issued by the master device 501 is first sent to the slave device 502, and then the slave device 502 interprets a corresponding timing signal according to the operation command to directly control the corresponding device. The slave device 502 reads device status data (usually analog) in real time or at intervals, and converts analog information into a digital signal and feeds it back to the master device 501.

Exemplarily, in an embodiment of the present disclosure, the system for controlling a dose further includes at least one encoder 507, the encoder 507 is electrically connected to the motor 504, the encoder 507 feeds back the movement position information of the source carrier 505 and/or the collimator 506 to the drive 503 and the slave device 502; and the timer 5021 receives the movement position information sent by the encoder 507, and sends the control instruction to the drive 503 based on the movement position information.

It should be noted that an embodiment of the present disclosure may also feed back the movement position information of the source carrier and/or the collimator to the timer of the drive and the slave device through other apparatuses, such as a position monitoring apparatus, or a position switch, which is not limited in the embodiments of the present disclosure. It is only used as an example for the encoder to feed back the movement position information of the source carrier and/or the collimator to the timer of the drive and the slave device, and it does not mean that the embodiments of the present disclosure is limited thereto. In the embodiments of the present disclosure, when determining the overlapping area between the source carrier and the collimator based on the movement position information of the source carrier and/or the collimator, there may be the following several achievable methods: in an achievable method, when the source carrier moves relative to the collimator, the timer receives the movement position information of the encoder of the motor of the source carrier; in another achievable method, when the collimator moves relative to the source carrier, the timer receives the movement position information of the encoder of the motor of the collimator; or in yet another achievable method, when the collimator and the source carrier move relative to each other, the timer receives the movement position information of the encoders of the motor of the source carrier and of the motor of the collimator separately or at the same time.

Embodiment 8

Based on the method for controlling a dose in radiotherapy described in Embodiment 1 to Embodiment 4 above, an embodiment of the present disclosure provides a computer storage medium, the computer storage medium storing a computer program, the computer program, when executed by a processor, implements the method for controlling a dose as described in Embodiment 1 to Embodiment 4.

The apparatus for controlling a dose of an embodiment of the present disclosure takes in various forms, including but not limited to:

(1) Mobile communication device: this type of device is characterized by mobile communication function, and its main goal is to provide voice and data communication. Such terminals include: smart phones (such as iPhone), multimedia cellphones, feature cellphones, low-end cellphones or the like.

(2) Ultra-mobile personal computer device: this type of device belongs to the category of personal computer, has computing and processing functions, and generally has mobile Internet access characteristics. Such terminals include: PDAs, MIDs, and UMPC devices, such as iPad.

(3) Portable entertainment equipment: this type of device may display and play multimedia content. Such devices include: audio and video players (such as iPod), hand-held game consoles, e-books, and smart toys and portable vehicle-mounted navigation devices.

(4) Other controllers with data interaction function.

So far, specific embodiments of the present subject matter have been described. Other embodiments are within the scope of the appended claims. In some cases, the actions recited in the claims may be performed in a different order and still achieve the desired result. In addition, the processes depicted in the accompanying drawings do not necessarily require the particular order or sequential order shown to achieve the desired result. In some embodiments, multitasking and parallel processing may be advantageous.

For the convenience of description, when describing the above apparatus, the functions are divided into various units and described separately. Of course, when implementing the present disclosure, the functions of the units may be implemented in the same or a plurality of software and/or hardware.

Those skilled in the art should understand that the embodiments of the present disclosure may be provided as a method, a system, or a computer program product. Therefore, the present disclosure may take the form of an entirely hardware embodiment, an entirely software embodiment, or an embodiment combining software and hardware aspects. Moreover, the present disclosure may take the form of a computer program product implemented on one or more computer-usable storage mediums (including but not limited to disk memory, CD-ROM, optical memory, etc.) containing computer-usable program codes.

The present disclosure is described with reference to flowcharts and/or block diagrams of the method, apparatus, and computer program product according to the embodiments of the present disclosure. It should be understood that each flow and/or block in the flowcharts and/or block diagrams, and combinations of flows and/or blocks in the flowcharts and/or block diagrams may be implemented by computer program instructions. These computer program instructions may be provided to a processor of a general-purpose computer, dedicated computer, embedded processor, or other programmable data processing devices to produce a machine, such that instructions executed by the processor of the computer or other programmable data processing devices produce an apparatus for implementing the functions specified in one or more flows in the flowcharts and/or one or more blocks in the block diagrams.

These computer program instructions may also be stored on a computer-readable memory capable of directing the computer or other programmable data processing devices to work in a specific method such that the instructions stored on the computer-readable memory produce a product that includes an instruction apparatus that implements the functions specified in one or more flows in the flowcharts and/or one or more blocks in the block diagrams.

These computer program instructions may also be loaded onto the computer or other programmable data processing devices, such that a series of operation steps may be performed on the computer or other programmable devices to produce a computer-implemented process, such that the instructions executed on the computer or other programmable devices provide steps for implementing the functions specified in one or more flows in the flowcharts and/or one or more blocks in the block diagrams.

In a typical configuration, a computing device includes one or more processors (CPUs), input/output interfaces, network interfaces, and memory.

The memory may include non-persistent memory, random access memory (RAM), and/or non-volatile memory in computer-readable medium, such as read-only memory (ROM) or flash read-only memory (flash RAM). Memory is an example of the computer-readable medium.

Computer-readable medium includes both permanent and non-persistent, removable and non-removable media. Information may be stored by any method or technology. Information may be computer-readable instructions, data structures, program modules, or other data. Examples of computer storage medium include, but are not limited to, phase-change random access memory (PRAM), static random access memory (SRAM), dynamic random access memory (DRAM), other types of random access memory (RAM), read-only memory (ROM), electrically erasable programmable read-only memory (EEPROM), flash memory or other memory technologies, read-only disc read-only memory (CD-ROM), digital versatile disc (DVD) or other optical storage, magnetic tape cartridges, magnetic tape, magnetic disk storage or other magnetic storage devices, or any other non-transmission medium that may be used to store information that can be accessed by the computing device. As defined herein, the computer-readable medium does not include temporary computer-readable media (transitory media) such as modulated data signals and source carrier waves.

It should also be noted that the terms "including," "comprising," or any other variation thereof are intended to encompass non-exclusive inclusion, such that a process, method, product, or device that includes a series of elements includes not only those elements but also other elements not explicitly listed, or those that are inherent to such process, method, product, or device. Without more restrictions, elements defined by the sentence "including a . . . " do not exclude the existence of other identical elements in the process, method, product or device including the said elements.

Those skilled in the art should understand that the embodiments of the present disclosure may be provided as a method, a system, or a computer program product. Therefore, the present disclosure may take the form of an entirely hardware embodiment, an entirely software embodiment, or an embodiment combining software and hardware aspects. Moreover, the present disclosure may take the form of a computer program product implemented on one or more computer-usable storage mediums (including but not limited to disk memory, CD-ROM, optical memory, etc.) containing computer-usable program codes.

The present disclosure may be described in the general context of computer-executable instructions executed by the computer, such as program modules. Generally, program modules include routines, programs, objects, components, data structures, etc. that perform specific transactions or implement specific abstract data types. The present disclosure may also be practiced in distributed computing environments in which transactions are executed by remote processing devices connected through communication networks. In a distributed computing environment, the program modules may be located in local and remote computer storage mediums including storage devices.

The embodiments in this specification are described in a progressive method, and the same or similar parts between the embodiments may refer to each other. Each embodiment focuses on the differences from other embodiments. In particular, for the system embodiment, since it is basically similar to the method embodiment, the description thereof is relatively simple. For related details, it may refer to the part of description in the method embodiment.

The above description is merely embodiments of the present disclosure and is not intended to limit the present disclosure. For those skilled in the art, the present disclosure may have various modifications and changes. Any modification, equivalent replacement, improvement, etc. made within the spirit and principle of the present disclosure shall be included in the scope of the claims of the present disclosure.

What is claimed is:

1. A method for controlling a radiation dose in radiotherapy of a patient, comprising:
   irradiating rays to a target area of the patient through a collimator; and
   keeping, after a source carrier starts to separate from the collimator in a process of controlling separation of the source carrier and the collimator, timing radiation of the rays or calculating the radiation dose of the rays such that the radiation dose of the rays received by the patient is equal to a radiation dose required for the radiotherapy.

2. The method according to claim 1, wherein
   keeping, after the source carrier starts to separate from the collimator in the process of controlling separation of the source carrier and the collimator, timing the radiation of the rays or calculating the radiation dose of the rays till a preset duration is reached after the source carrier starts to separate from the collimator.

3. The method according to claim 1, wherein
   keeping, after the source carrier starts to separate from the collimator in the process of controlling separation of the source carrier and the collimator, timing the radiation of the rays or calculating the radiation dose of the rays till an overlapping area between the source carrier and the collimator is equal to or less than a second preset threshold.

4. The method according to claim 1, the method further comprising:
   starting to time the radiation of the rays or calculate the radiation dose of the rays before the source carrier is aligned with the collimator in the process of alignment of the source carrier and the collimator.

5. The method according to claim 4, wherein
   starting to time the radiation of the rays before the source carrier is aligned with the collimator in the process of alignment of the source carrier and the collimator and ending timing the radiation of the rays till a preset duration is reached after the source carrier starts to separate from the collimator in the process of controlling separation of the source carrier and the collimator such that the radiation dose of the rays received by the patient is equal to the radiation dose required for the radiotherapy; or
   starting to calculate the radiation dose of the rays before the source carrier is aligned with the collimator in the process of alignment of the source carrier and the collimator and ending calculating the radiation dose of the rays till a preset duration is reached after the source carrier starts to separate from the collimator in the process of controlling separation of the source carrier and the collimator such that the radiation dose of the rays received by the patient is equal to the radiation dose required for the radiotherapy.

6. The method according to claim 4, wherein
starting to time the radiation of the rays before the source carrier is aligned with the collimator in the process of alignment of the source carrier and the collimator and ending timing the radiation of the rays when an overlapping area between the source carrier and the collimator reaches a second preset threshold in the process of controlling separation of the source carrier and the collimator such that the radiation dose of the rays received by the patient is equal to the radiation dose required for the radiotherapy; or
starting to calculate the radiation dose of the rays before the source carrier is aligned with the collimator in the process of alignment of the source carrier and the collimator and ending calculating the radiation dose of the rays when an overlapping area between the source carrier and the collimator reaches a second preset threshold such that the radiation dose of the rays received by the patient is equal to the radiation dose required for the radiotherapy.

7. The method according to claim 4, wherein
starting to time the radiation of the rays or calculate the radiation dose of the rays when an overlapping area between the source carrier and the collimator reaches a first preset threshold.

8. The method according to claim 4, wherein
calculating the radiation dose of the rays received by the patient and determining whether the radiation dose of the rays received by the patient is equal to the radiation dose required for the radiotherapy.

9. The method according to claim 4, wherein the calculating the radiation dose of the rays received by the patient comprises at least one of:
determining and calculating, based on a radiation dose of a first ray corresponding to an overlapping area between the source carrier and the collimator, a radiation dose of rays from a timing start time to a timing end time in the process of alignment of the source carrier and the collimator; and
determining and calculating, based on a radiation dose of a second ray corresponding to an overlapping area between the source carrier and the collimator, the radiation dose of rays from a timing start time to a timing end time in the process of controlling separation of the source carrier and the collimator.

10. The method according to claim 9, wherein the radiation dose of the first ray corresponding to the overlapping area between the source carrier and the collimator is specifically:
in the process of alignment of the source carrier and the collimator, when the overlapping area between the source carrier and the collimator is A % of a full overlapping area, a radiation dose rate is x1% of a dose rate for the full overlapping area, x1 and A are positive integers, and the full overlapping area refers to an overlap area between the source carrier and the collimator when a collimating hole of the collimator is in-line with a radiation channel of the source carrier; and
the radiation dose of the second ray corresponding to the overlapping area between the source carrier and the collimator is specifically:
in the process of controlling the separation of the source carrier and the collimator, when the overlapping area between the source carrier and the collimator is B % of the full overlapping area, a radiation dose rate is y1% of the dose rate for the full overlapping area, and y1 and B are positive integers.

11. The method according to claim 10, wherein the radiation dose of the first ray corresponding to the overlapping area between the source carrier and the collimator is specifically:
the overlapping area between the source carrier and the collimator reaches the first preset threshold, and the corresponding radiation dose rate is x % of the dose rate for the full overlapping area, and x is a positive integer;
the overlapping area between the source carrier and the collimator reaches the second preset threshold, and the corresponding radiation dose rate is y % of the dose rate for the full overlapping area, and y is a positive integer.

12. The method according to claim 1, the method further comprising:
receiving a radiotherapy plan and performing radiotherapy according to an irradiation modality set in the radiotherapy plan, wherein the radiotherapy plan comprises radiation time for a plurality of different collimators or the radiation dose required for the radiotherapy.

13. A controller, comprising: a processor and a memory, a computer program being stored on the memory; the processor being configured to execute the computer program stored on the memory to:
keep, after a source carrier starts to separate from a collimator in a process of controlling separation of the source carrier and the collimator, timing radiation of the rays or calculating radiation dose of the rays such that a radiation dose of the rays received by the patient is equal to a radiation dose required for the radiotherapy.

14. The controller according to claim 13, wherein the processor is configured to execute the computer program stored on the memory to:
start to time the radiation of the rays or calculate the radiation dose of the rays before the source carrier is aligned with the collimator in the process of alignment of the source carrier and the collimator.

15. The controller according to claim 14, wherein the processor is configured to execute the computer program stored on the memory to:
start to time the radiation of the rays before the source carrier is aligned with the collimator in the process of alignment of the source carrier and the collimator and end timing the radiation of the rays till a preset duration is reached after the source carrier starts to separate from the collimator in the process of controlling separation of the source carrier and the collimator such that the radiation dose of the rays received by the patient is equal to the radiation dose required for the radiotherapy; or
start to calculate the radiation dose of the rays before the source carrier is aligned with the collimator in the process of alignment of the source carrier and the collimator and end calculating the radiation dose of the rays till a preset duration is reached after the source carrier starts to separate from the collimatorin the process of controlling separation of the source carrier and the collimator such that the radiation dose of the rays received by the patient is equal to the radiation dose required for the radiotherapy.

16. The controller according to claim 14, wherein the processor is configured to execute the computer program stored on the memory to:

start to time the radiation of the rays before the source carrier is aligned with the collimator in the process of alignment of the source carrier and the collimator and end timing the radiation of the rays when an overlapping area between the source carrier and the collimator reaches a second preset threshold in the process of controlling separation of the source carrier and the collimator such that the radiation dose of the rays received by the patient is equal to a radiation dose required for the radiotherapy; or start to calculate the radiation dose of the rays before the source carrier is aligned with the collimator in the process of alignment of the source carrier and the collimator and end calculating the radiation dose of the rays when the overlapping area between the source carrier and the collimator reaches a second preset threshold such that the radiation dose of the rays received by the patient is equal to a radiation dose required for the radiotherapy.

17. The controller according to claim 14, wherein the processor is configured to execute the computer program stored on the memory to: start to time the radiation of the rays or calculate the radiation dose of the rays when an overlapping area between the source carrier and the collimator reaches a first preset threshold.

18. The controller according to claim 14, wherein the processor is configured to execute the computer program stored on the memory to: calculate the radiation dose of the rays received by the patient and determine whether the radiation dose of the rays received by the patient is equal to the radiation dose required for the radiotherapy.

19. A system for controlling a dose in radiotherapy of a patient, comprising: a master device, a slave device, at least one drive, and at least one motor; wherein the master device and the slave device are in communication connection, the master device comprises a user interface, and the master device is configured to receive a user operation command and send the user operation command to the slave device;

the slave device comprises at least one controller according to claim 13, and the controller is configured to send a control instruction to the at least one drive according to the user operation command;

the drive is connected to the motor, the drive is configured to send the control instruction to the motor, the motor is configured to drive a source carrier and/or a collimator to move according to the control instruction, so that a radiation channel in the source carrier is aligned with or separated from a collimating hole in the collimator.

20. A computer storage medium, the computer storage medium storing a computer program, the computer program, when executed by a processor, implements the method for controlling a dose according to claim 1.

* * * * *